United States Patent [19]

Patel

[11] 4,205,691

[45] Jun. 3, 1980

[54] HEMOSTATIC CATHETER AND METHOD

[75] Inventor: Bhupendra C. Patel, Elgin, Ill.

[73] Assignee: The Kendall Company, Boston, Mass.

[21] Appl. No.: 951,811

[22] Filed: Oct. 16, 1978

Related U.S. Application Data

[62] Division of Ser. No. 791,668, Apr. 28, 1977, Pat. No. 4,133,303.

[51] Int. Cl.² ............................................. A61M 25/00
[52] U.S. Cl. ................................ 128/774; 128/349 B
[58] Field of Search ........ 128/349 R, 349 B, 349 BV, 128/351; 116/266; 73/141 A; 33/147 B, 148 D

[56] References Cited

U.S. PATENT DOCUMENTS

| | | | |
|---|---|---|---|
| 2,825,224 | 3/1958 | Lindenauer | 272/135 X |
| 4,016,885 | 4/1977 | Bruner | 128/349 |

FOREIGN PATENT DOCUMENTS 790091  11/1935  France ....................................... 128/25

*Primary Examiner*—Stephen C. Pellegrino
*Attorney, Agent, or Firm*—Powell L. Sprunger

[57] ABSTRACT

A hemostatic catheter having an elongated shaft of elastic material, and an inflatable balloon adjacent a distal end of the shaft. The catheter measures longitudinal expansion in a portion of the shaft when force is applied against the catheter to provide an indication of the amount of tension in the catheter shaft.

2 Claims, 16 Drawing Figures

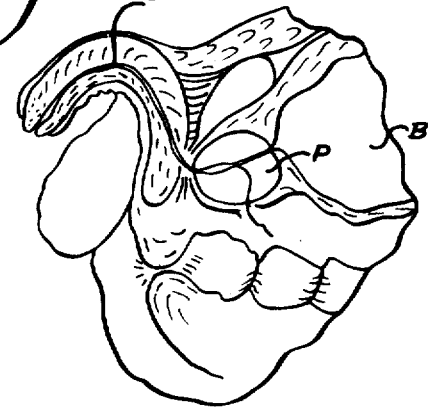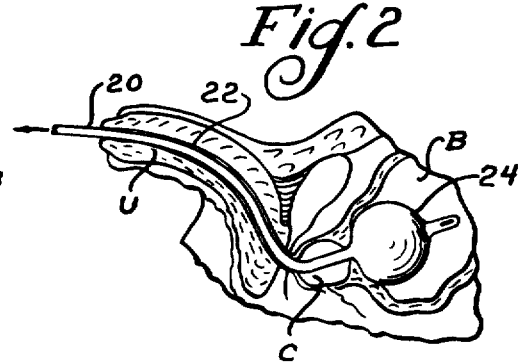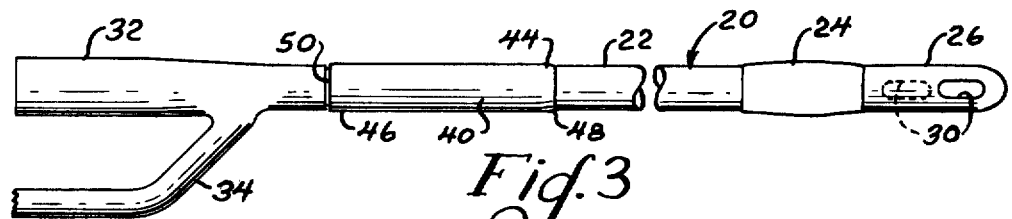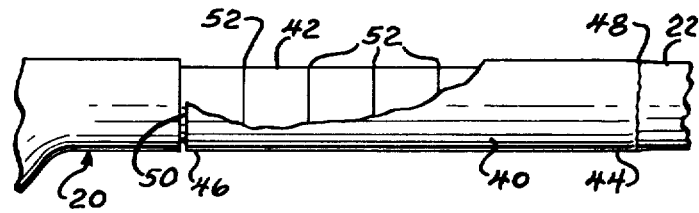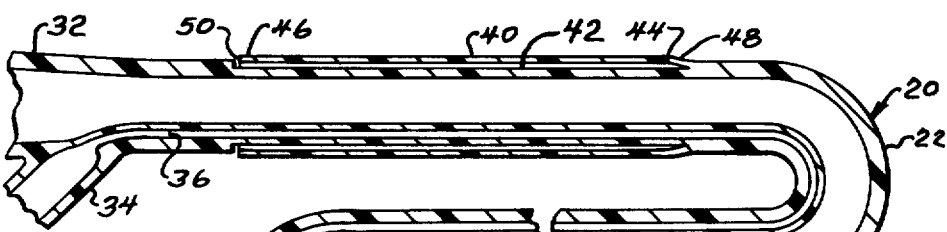

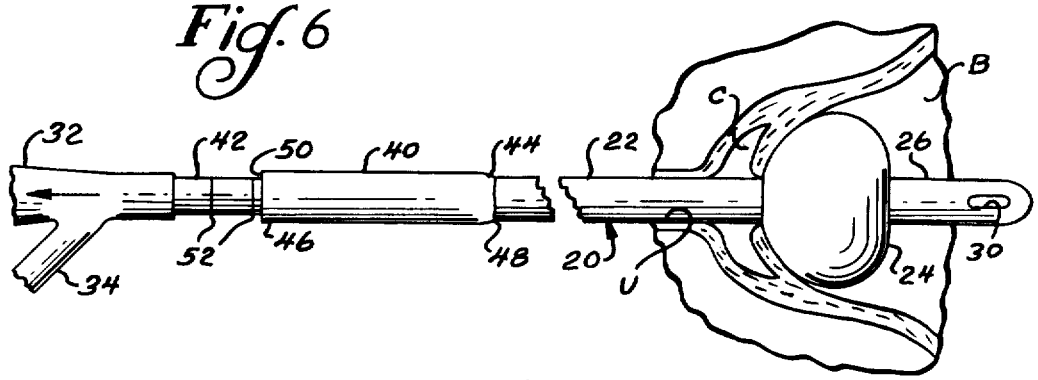
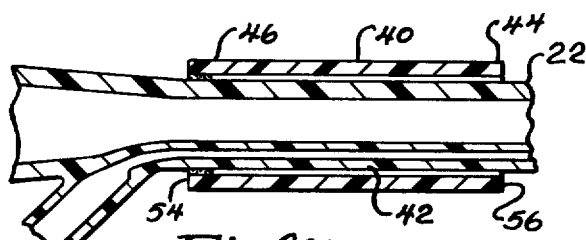
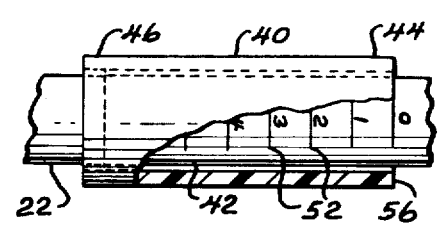
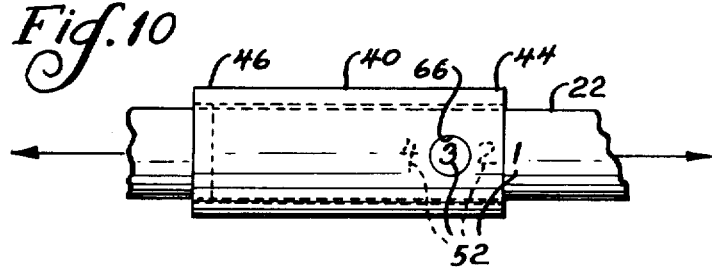

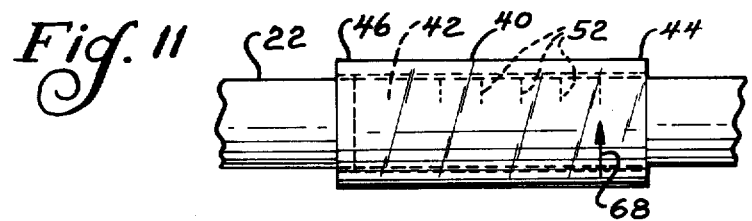
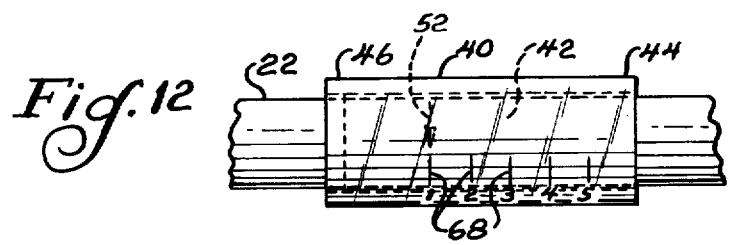
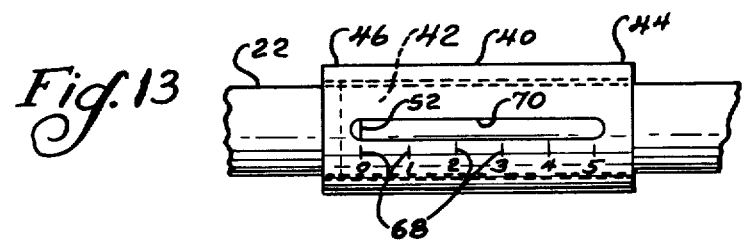
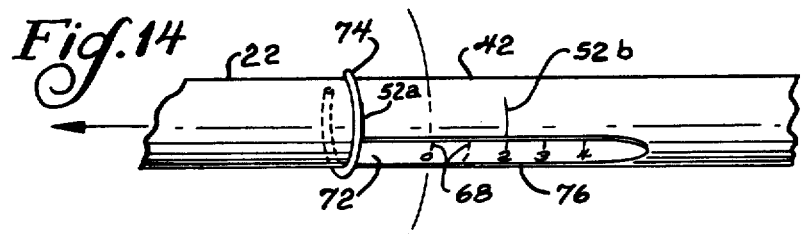
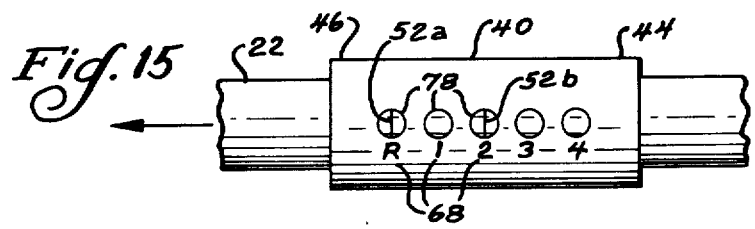
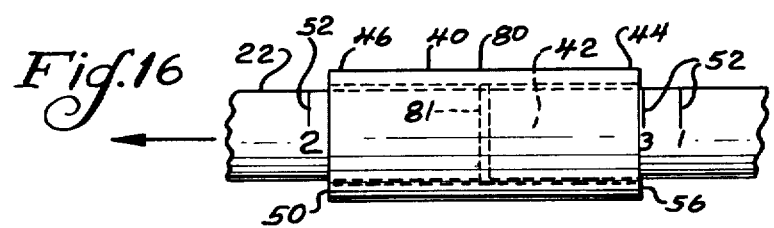

HEMOSTATIC CATHETER AND METHOD

This is a division of application Ser. No. 791,668 filed Apr. 28, 1977, now U.S. Pat. No. 4,133,303.

BACKGROUND OF THE INVENTION

The present invention relates to catheters, and more particularly to hemostatic catheters.

In certain male patients it may be necessary to remove the prostate in the event that it becomes fibroid or cancerous. Generally, the prostate is removed either through a suprapubic procedure or a transurethral dissection during which a cystoscope is utilized to carve out the prostate. After the prostate has been removed, the cystoscope is withdrawn from the patient leaving a bleeding cavity or prostatic fossa adjacent the bladder where the prostate was formerly located.

In the past, the urologists have stopped the bleeding over a period of time in the following manner. A catheter having a balloon adjacent a distal end of the catheter shaft is passed through the urethra until the balloon is located in the bladder and a proximal end of the catheter is located outside the patient. The removed prostate is weighed to estimate the size of the prostatic fossa in the particular patient, and a quantity of fluid proportional to the prostatic weight is pumped into the catheter balloon in order to inflate the balloon in the bladder a sufficient amount to later prevent the balloon from falling into the prostatic fossa. Next, force is applied against the catheter shaft such that the balloon in turn applies pressure against the apex of the incised blood vessels, with the pressure being maintained for a period of time which may vary from five minutes to twenty four hours depending upon the preference of the particular urologist. The amount of force applied to the catheter by pulling its proximal end also varies with the urologist, but is believed equivalent to the force caused by a weight in the range of from 1–12 lbs. if such weight was attached to the proximal end of the catheter.

In this manner the bleeding is eventually stopped, although the procedure is accompanied by a great amount of uncertainty. Initially, the urologist does not have any clear indication from experience concerning the amount of force which is desired to stop bleeding, and, even if known, the urologist could not determine whether the desired amount of force is being applied to accomplish hemostasis unless actual weights are attached to the proximal end of the catheter shaft. In this regard, it is necessary to apply sufficient force against the catheter to obtain hemostasis, yet undue pressure by the inflated balloon against the blood vessels in the bladder may result in pressure necrosis and must be prevented.

Thus, it is desirable to provide the urologist with a convenient indication of the applied forces and pressures, in order that he can determine through experience the proper range of forces required for hemostatis while preventing pressure necrosis in the bladder. Once such range has been ascertained, it is desirable that the urologist may readily determine whether the proper amount of force is being applied against the catheter during a particular procedure without the inconvenience of hanging weights from the catheter.

SUMMARY OF THE INVENTION

A principal feature of the present invention is the provision of an improved hemostatic catheter.

The catheter of the present invention comprises an elongated shaft of elastic material, an inflatable balloon adjacent a distal end of the shaft, and means for measuring longitudinal expansion of the catheter shaft responsive to application of force against a proximal portion of the catheter. The catheter shaft may be passed through the patient's urethra and the balloon may be inflated in the patient's bladder after prostatectomy.

A feature of the present invention is that the measuring means provides a measure of the amount of tension in the catheter shaft after application of force to the proximal end portion of the catheter.

Another feature of the present invention is that the measured amount of tension in the catheter shaft provides an indication of the amount of pressure applied by the inflated balloon against the bladder.

Thus, a feature of the present invention is that the amount of pressure applied by the balloon against the bladder may be readily determined and controlled through use of the catheter measuring means in order to accomplish hemostasis in the prostatic fossa.

Still another feature is that the hemostatic catheter of the present invention is of simplified construction and convenient in use.

Another feature of the present invention is the provision of a method for accomplishing hemostasis after prostatectomy.

Further features will become more fully apparent in the following description of the embodiments of this invention and from the appended claims.

DESCRIPTION OF THE DRAWINGS

In the drawings:

FIG. 1 is a fragmentary diagrammatic view of a patient's body;

FIG. 2 is a diagrammatic view of the patient's body illustrating a hemostatic catheter positioned to accomplish hemostasis in the prostatic fossa after prostatectomy;

FIG. 3 is a fragmentary elevational view of a hemostatic catheter of the present invention;

FIG. 4 is a fragmentary elevational view, partly broken away, of the catheter of FIG. 3;

FIG. 5 is a fragmentary sectional view of the catheter of FIG. 3;

FIG. 6 is a fragmentary elevational view of the catheter of FIG. 3 illustrating use of the catheter to accomplish hemostasis;

FIG. 7 is a fragmentary sectional view of another embodiment of the present invention;

FIG. 8 is a fragmentary elevational view, partly broken away, of the catheter of FIG. 7;

FIG. 9 is a sectional view of another embodiment of the present invention;

FIG. 10 is a fragmentary elevational view of another embodiment of the present invention;

FIG. 11 is a fragmentary elevational view of another embodiment of the present invention;

FIG. 12 is a fragmentary elevational view of another embodiment of the present invention;

FIG. 13 is a fragmentary elevational view of another embodiment of the present invention;

FIG. 14 is a fragmentary perspective view of another embodiment of the present invention;

FIG. 15 is a fragmentary elevational view of another embodiment of the present invention; and FIG. 16 is a fragmentary elevational view of another embodiment of the present invention.

DESCRIPTION OF THE PREFERRED EMBODIMENTS

Referring now to FIGS. 3-5, there is shown a hemostatic catheter generally designated 20 having an elongated shaft 22 of flexible and elastic material, such as latex rubber or silicone. The catheter 20 has an inflatable balloon 24 of flexible material secured to the shaft 22 adjacent a distal end 26 of the catheter 20, a drainage lumen 28 extending between one or more drainage eyes 30 adjacent the distal end 26 of the shaft 22 and a proximal end 32 of the catheter. The catheter 20 also has a side arm 34 adjacent the proximal end 32 of the catheter 20, and an inflation lumen 36 communicating between valve means (not shown) on the side arm 34 and a cavity 38 intermediate the balloon 24 and an outer surface of the shaft 22.

As shown, the catheter 20 has an elongated sleeve 40 overlying a longitudinal section 42 of the catheter shaft 22 adjacent a proximal end of the shaft 22. The sleeve 40 has a first end portion 44 secured to the shaft 22 at a point 48, and a free second end portion 46 located proximal the first end portion 44, such that the sleeve 40 extends proximally from the first end portion 44 toward the proximal end 32 of the catheter 20. The sleeve may be made from a flexible or relatively rigid material, as desired. In a preferred form, as shown, the sleeve 40 may comprise an integral extension of the catheter shaft 22 with the sleeve 40 being free of attachment form the catheter shaft 22 intermediate the connecting point 48 and a reference end edge 50 defined by the second end portion 46 of the sleeve 40. As shown in FIG. 4, the longitudinal section 42 of the catheter shaft 22 has a plurality of longitudinally spaced reference markings or indicia 52 located beneath the sleeve 40 in the normal relaxed configuration of the catheter 20.

With reference to FIG. 1, during prostatectomy the prostate P of a male patient is removed either suprapubically or by transurethral dissection, causing bleeding in the corresponding cavity or prostatic fossa C, illustrated in FIG. 2, defined by the removed prostate. In order to stop bleeding (hemostasis) in the prostatic fossa C, the hemostatic catheter 20 is passed through the patient's urethra U until the balloon 24 is located in the patient's bladder B where it is inflated, after which forces are applied against the proximal end of the catheter 20 which are transmitted through the catheter shaft 22 to the balloon 24. In turn, the inflated balloon 24 applies pressure against the apex of the incised blood vessels in the prostatic fossa C eventually causing hemostasis in the prostatic fossa C. During this time, it is desirable to know that the pressure applied by the balloon is sufficiently large to stop bleeding yet sufficiently small to minimize the possibility of pressure necrosis in the bladder which otherwise might be caused by excessive balloon pressure.

As shown in FIG. 6, the elastic catheter shaft 22 expands in a longitudinal direction responsive to the force applied against the catheter, such that the longitudinal shaft section 42 increases in length relative the sleeve 40, thus exposing one or more of the indicia or reference markings 52 outside the reference edge 50 of the sleeve 40. In this manner, the amount of tension in the shaft may be determined by the number of reference markings 52 located outside the sleeve 40 after application of the force, with the reference markings 52 being appropriately calibrated in order that an accurate determination of the applied force and resulting balloon pressure may be made. Thus, the sleeve 40 and longitudinal section 42 cooperate to measure an increase in length or expansion of the longitudinal section 42 responsive to increased tension in the catheter shaft 22. The urologist may utilize the catheter of the present invention to determine the range of applied force desired to accomplish hemostasis after prostatectomy without causing pressure necrosis in the bladder. Once known, the urologist can establish the desired amount of applied force and balloon pressure through use of the reference markings 52 relative the reference edge 50 of the sleeve 40, and the proximal end 32 of the stressed catheter may then be secured to the patient's thigh with the desired amount of tension in the catheter shaft resulting in hemostasis through a period of time while maintaining the possibility of pressure necrosis.

Thus, the catheter of the present invention permits an accurate determination of the amount of forces applied against the catheter shaft and the resulting pressures caused by the inflated balloon against the bladder. The proper range of pressures may be determined in order to obtain hemostasis without necrosis, and the pressure ranges may be readily reproduced in subsequent procedures through use of the catheter.

Another embodiment of the present invention is illustrated in FIGS. 7 and 8, in which like reference numerals designate like parts. In this embodiment, the second end portion 46 of the sleeve 40 is secured to the catheter shaft 22 by suitable means, such as by adhesive 54, while the first end portion 44 is free of attachment from the catheter shaft 22 and defines a reference end edge 56 of the sleeve 40. As before, the longitudinal section 42 has a plurality of longitudinally spaced reference markings or indicia 52 located beneath the sleeve 40 when the catheter shaft 22 is in a relaxed state. When forces are applied to the proximal end of the catheter the section 42 of the catheter shaft 22 expands in a longitudinal direction, and the reference end edge 56 may be utilized in association with the aligned reference markings or indicia 52 to provide an indication of the amount of tension in the catheter shaft 22. In this manner, the amount of pressure applied by the inflated balloon against the bladder may be determined, as previously described. The sleeve 40 may be made from an opaque or transparent material, as desired.

Another embodiment of the present invention is illustrated in FIG. 9, in which like reference numerals designate like parts. In this embodiment, the sleeve 40 is located over a flexible conduit 58 in an adapter 60. The adapter 60 has a first connector 62 at one end which may be positioned and clamped in a proximal end of a catheter, and a second connector 64 adjacent an opposed end of the adapter 60 which may be secured to a drainage tube communicating with a suitable collection bag (not shown) for retaining urine which drains through the catheter, adapter and drainage tube to the bag. The conduit 58 of the adapter 60 is made from an elastic material and has indicia disposed beneath the sleeve 40, such that the amount of tension in the conduit 58 may be determined in a manner as previously described through use of the reference edge 56 relative the indicia on the conduit 58 after application of force to the downstream end of the adapter 60 adjacent the second connector 64. Of course, the adapter or drainage tube itself may include any of the tension indicating devices described herein.

Another embodiment of the present invention is illustrated in FIG. 10, in which like reference numerals designate like parts. In this embodiment, the second end portion 46 of the sleeve 40 is secured to the catheter shaft 22 while the first end portion 44 is free of attachment from the catheter shaft, and the sleeve 40 includes an aperture 66 through which the shaft indicia 52 may be viewed after application of force against the proximal end of the catheter. Thus, during use, the reference marking or numeral 52 associated with a particular level of tension in the catheter shaft 22 becomes aligned with the sleeve aperture or window 66. In other respects, the conduit of FIG. 10 operates in a manner as previously described in connection with the catheter of FIGS. 3-6.

Another embodiment of the present invention is illustrated in FIG. 11, in which like reference numerals designate like parts. In this embodiment, the second end portion 46 is secured to the catheter shaft 22, while the first end portion 44 is free of attachment from the catheter shaft 22. Also, in this embodiment, the sleeve 40 is made from a transparent material, such as a suitable plastic. The sleeve 40 includes a reference marking 68 while the longitudinal section 42 of the catheter shaft 22 includes a plurality of longitudinally spaced reference markings 52 disposed beneath the sleeve 40 when the catheter shaft is in a relaxed condition. Accordingly, when forces are applied against the proximal end of the catheter, the reference marking 68 of the sleeve and the indicia 52 of the catheter shaft may be utilized to determine the amount of tension in the catheter shaft depending upon alignment of a particular reference marking 52 with the reference marking 68.

Another embodiment of the present invention is illustrated in FIG. 12, in which like reference numerals designate like parts. In this embodiment, the second end portion 46 of the sleeve is secured to the catheter shaft 22 while the first end portion 44 is free of attachment from the catheter shaft 22. Also, in this embodiment, the sleeve 40 includes a plurality of longitudinally spaced reference markings or indicia 68, while the longitudinal section 42 of the shaft 22 includes a reference marking 52 located beneath the sleeve 40. In this embodiment, the sleeve 40 is made from a transparent material, such as plastic, and alignment of the reference marking 52 on the longitudinal shaft section 42 may be ascertained relative the reference markings 68 on the sleeve 40 in order to determine the amount of tension in the shaft 22.

Another embodiment of the present invention is illustrated in FIG. 13, in which like reference numerals designate like parts. In this embodiment, the second end portion 46 of the sleeve 40 is attached to the catheter shaft 22, while the first end portion 44 is free of attachment from the shaft. As shown, the sleeve 40 includes an elongated opening or cutout 70 with a plurality of spaced indicia 68 being disposed longitudinally along the opening 70. Also, the longitudinal section 42 of the catheter shaft 22 has a reference marking 52, such that the amount of tension in the catheter shaft 22 may be determined by alignment of the reference markings 52 relative the reference markings 68.

Another embodiment of the present invention is illustrated in FIG. 14, in which like reference numerals designate like parts. In this embodiment, the reference device comprises a clip 72 having a ring portion 74 which may be releasably secured onto the catheter shaft 22. The clip 72 also has an elongated arm 76 which extends longitudinally along the shaft 22 from the ring portion 74. As shown, the arm 76 of the clip 72 has a plurality of longitudinally spaced indicia or reference markings 68, while the longitudinal section 42 of the catheter shaft 22 has a first reference marking 52a and a longitudinally spaced second reference marking 52b. In use, the clip 72 is positioned on the shaft 22 with the ring portion 74 being aligned with the first reference marking 52a on the catheter shaft. When forces are applied against the proximal end of the catheter shaft, ring portion 74 of the clip 72 remains in position at the first reference marking 52a of the catheter shaft, and alignment of the second reference marking 52b relative the indicia 68 indicates the amount of tension in the catheter shaft.

Another embodiment of the present invention is illustrated in FIG. 15, in which like reference numerals designate like parts. In this embodiment, the sleeve 40 is slidably received on the catheter shaft 22, and the sleeve 40 has a plurality of longitudinally spaced apertures 78 with indicia 68 on the sleeve 40 being associated with each of the apertures 78. As shown, the catheter shaft 22 has first and second longitudinally spaced reference markings 52a and 52b. In use, the reference marking 52a on the shaft 22 is aligned with the sleeve aperture or window 68 designated by the reference marking "R," and the second end portion 46 of the sleeve 40 may be secured in place on the catheter shaft through use of suitable means, such as tape. The amount of tension in the catheter shaft may be determined by alignment of the second reference marking 52b in the sleeve apertures 78 through which the reference marking 52b is viewed.

Another embodiment of the present invention is illustrated in FIG. 16, in which like reference numerals designate like parts. In this embodiment, a central portion 80 of the sleeve 40 is secured to the catheter shaft 22 by suitable means, such as adhesive 81. The longitudinal section 42 of the catheter shaft 22 has longitudinally spaced indicia or reference markings 52 on both longitudinal sides of the sleeve central portion 80. In use, the shaft section 42 expands in a longitudinal direction on both sides of the sleeve central portion 80 responsive to increased tension in the shaft. Thus, opposed end edges 50 and 56 of the sleeve may be utilized as reference positions relative the shaft indicia or reference markings 52 on the opposed sides of the sleeve central portion 80 in order to determine the amount of tension in the catheter shaft.

According to a method of the invention, hemostasis is accomplished in a patient after prostatectomy by placing a catheter in the patient's urethra with the catheter balloon located in the patient's bladder, after which the balloon is inflated in the patient's bladder. Forces are then applied against a proximal portion of the catheter while measuring longitudinal expansion in the shaft to provide an indication of a desired amount of tension in the catheter shaft.

According to another method of the present invention a desired amount of tension in conduit means is determined during a procedure on a patient by placing and retaining a distal portion of the conduit means in the patient's body with an elastic portion of the conduit means located outside the patient's body. Forces are then applied to the conduit means including the elastic portion while determining longitudinal distortion in the elastic portion to provide an indication of the tension in the conduit means.

The foregoing detailed description is given for clearness of understanding only, and no unnecessary limitations should be understood therefrom, as modifications will be obvious to those skilled in the art.

I claim:

1. An adapter for a catheter comprising, an elongated tubular portion of elastic material having a substantially uniform diameter, a pair of connecting portions defining opposed ends of the adapter, and an indicating means secured to the adapter and overlying the tubular portion, with said tubular portion moving longitudinally relative to the indicating means to point out differing surface portions of of the tubular portion responsive to stretching of the tubular portion and an increase of tension in said tubular portion without inflation of the tubular portion.

2. In a tension device for a patient, comprising:

a catheter having an elongated shaft, retention means adjacent a distal end of the catheter, and a proximal end; the improvement comprising:

an adapter having an elongated tubular portion of elastic material, a distal connecting portion defining a distal end of the adapter and being adapted for attachment to said proximal end of the catheter, such that tension applied to the tubular portion is transmitted to the catheter shaft through the proximal end of the attached catheter, and an indicating means secured to the device and overlying the adapter tubular portion, with said tubular portion moving longitudinally relative to the indicating means to point out differing surface portions of the tubular portion responsive to stretching of the tubular portion and an increase of tension in said tubular portion to determine tension in the stretched tubular portion without inflation of the tubular portion.

* * * * *